(12) United States Patent
Lima et al.

(10) Patent No.: US 6,365,379 B1
(45) Date of Patent: Apr. 2, 2002

(54) ZINC FINGER PEPTIDE CLEAVAGE OF NUCLEIC ACIDS

(75) Inventors: Walt F. Lima, San Diego; Stanley T. Crooke; Muthiah Manoharan, both of Carlsbad, all of CA (US)

(73) Assignee: ISIS Pharmaceuticals, Inc., Carlsbad, CA (US)

( * ) Notice: Subject to any disclaimer, the term of this patent is extended or adjusted under 35 U.S.C. 154(b) by 0 days.

(21) Appl. No.: 09/412,499

(22) Filed: Oct. 5, 1999

Related U.S. Application Data (60) Provisional application No. 60/103,309, filed on Oct. 6, 1998.

(51) Int. Cl.⁷ .......................... C12P 21/06; C12N 1/20; C12N 15/00; C07H 21/04; A61K 38/00
(52) U.S. Cl. ............... 435/91.3; 435/252.3; 435/320.1; 435/199; 536/23.1; 530/324
(58) Field of Search .............................. 435/91.3, 252.3, 435/320.1, 69.1, 199; 536/23.1; 530/324

(56) References Cited

U.S. PATENT DOCUMENTS

| | | | |
|---|---|---|---|
| 5,789,538 A | 8/1998 | Rebar et al. | 530/324 |
| 5,928,941 A | 7/1999 | Lee et al. | 435/325 |

OTHER PUBLICATIONS

Bai et al. Mol. Cell. Biol. (1996), 16(12), 6661–67, 1996.*
Barbier, B. et al., "Conformation–Controlled Hydrolysis of Polyribonucleotides by Sequential Basic Polypeptides," *J. Am. Chem. Soc.*, 1992, 114(9), 3511–3515.
Blackburn, P. et al., "Pancreatic Ribonuclease," in *The Enzymes*, 3rd Ed., Boyer, P.D. (ed.), Academic Press, N.Y., 1982, vol. 15, Chapter 12, 317–433.
Del Rosario, E. J. et al., "Kinetic and Equilibrium Studies of the Ribonuclease–Catalyzed Hydrolysis of Uridine 2',3'–Cyclic Phosphate," *Biochem.*, 1969, 8(5), 1884–1889.
Grubbs, R.H. et al., "Recent advances in olefin Metathesis and Its Application in Organic Synthesis," *Tetrahedron*, 1998, 54, 4413–4450.
Häner, R. et al., "The Sequence–Specific Cleavage of RNA by Artificial Chemical Ribonucleases," *Antisense and Nucleic Acid Drug Development*, 1997, 7, 423–430.
Herries, D. G. et al., "The Active Site and Mechanism of Action of Bovine Pancreatic Ribonuclease," *Biochem. J.*, 1962, 85, 127–134.
Ikehara, M. et al., "Inquiries into the structure–function relationship of ribonuclease T1 using chemically synthesized coding sequences," *Proc. Natl. Acad. Sci. U.S.A.*, 1986, 83, 4695–4699.
Lima, W.F. et al., "Highly efficient endonucleolytic cleavage of RNA by a $Cys_2His_2$ zinc–finger peptide," *Proc. Natl. Acad. Sci. USA*, 1999, 96, 10010–10015.
Manoharan, M. et al., "2'–O– and 3'–O–Pyrimidine Aminothether–Containing Oligonucleotides: Synthesis and Conjugation Chemistry", *Tetrahedron Letts.*, 1995, 3647–3650.
Page, D. C. et al., "The Sex–Determining Region of the Human Y Chromosome Encodes a Finger Protein," *Cell*, 1987, 51, 1091–1104.
Roberts, G. C. K. et al., "The Mechanism of Action of Ribonuclease," *Proc. Natl. Acad. Sci. U.S.A.*, 1969, 62, 1151–1158.
Takahashi, K. et al., Ribonuclease $T_1$, in *The Enzymes*, 3rd Ed., Boyer, P.D. (ed.), Academic Press, N.Y., 1982, vol. 15, Chapter 13, 435–468.
Tung, C–H. et al., "Design of peptide–acridine mimics of ribonuclease activity," *Proc. Natl. Acad. Sci. U.S.A.*, 1992, 89, 7114–7118.
Weiss, M. A. et al., "Alternating Zinc Finger Motifs in the Male–Associated Protein ZFY: Defining Architectural Rules by Mutagenesis and Design of an "Aromatic Swap" Second–Site Revertant," *Biochem.*, 1990, 29, 9808–9813.
Xiang, Q. et al., "Sequence Specificity of a Group II Intron Ribozyme: Multiple Mechanisms for Promoting Unusually High Discrimination against Mismatched Targets," *Biochem.*, 1998, 37, 3839–3849.

* cited by examiner

Primary Examiner—Ponnathapuachuta Murthy
Assistant Examiner—Tekchand Saidha
(74) Attorney, Agent, or Firm—Woodcock Washburn LLP (57) ABSTRACT

Selective cleavage of single stranded nucleic acids can be effected by contacting the nucleic acid with a zinc finger peptide in dimeric form. Dimerization results from diminution or elimination of zinc from the peptide, such that easily controllable and highly selective cleavage may be realized.

13 Claims, 8 Drawing Sheets

SEQUENCE LISTING

<160> NUMBER OF SEQ ID NOS: 11

<210> SEQ ID NO 1
<211> LENGTH: 30
<212> TYPE: PRT

```
<213> ORGANISM: Artificial Sequence
<220> FEATURE:
<223> OTHER INFORMATION: Description of Artificial Sequence: Novel
      Sequence

<400> SEQUENCE: 1

Lys Glu Lys Ser His Lys Thr Lys Ile His Thr Lys Leu Asn Ser Ser
  1               5                  10                  15

Asp Ala Ser Arg Tyr Glu Cys Tyr Gln Cys Gln Tyr Thr Lys
             20                  25                  30

<210> SEQ ID NO 2
<211> LENGTH: 19
<212> TYPE: RNA
<213> ORGANISM: Artificial Sequence
<220> FEATURE:
<223> OTHER INFORMATION: Description of Artificial Sequence: Novel
      Sequence

<400> SEQUENCE: 2
cuccaccaua guacacucc                                                        19

<210> SEQ ID NO 3
<211> LENGTH: 20
<212> TYPE: RNA
<213> ORGANISM: Artificial Sequence
<220> FEATURE:
<223> OTHER INFORMATION: Description of Artificial Sequence: Novel
      Sequence

<400> SEQUENCE: 3
acuccaccau aguacacucc                                                       20

<210> SEQ ID NO 4
<211> LENGTH: 16
<212> TYPE: RNA
<213> ORGANISM: Artificial Sequence
<220> FEATURE:
<223> OTHER INFORMATION: Description of Artificial Sequence: Novel
      Sequence

<400> SEQUENCE: 4
ggcgccgucg gugugg                                                           16

<210> SEQ ID NO 5
<211> LENGTH: 24
<212> TYPE: RNA
<213> ORGANISM: Artificial Sequence
<220> FEATURE:
<223> OTHER INFORMATION: Description of Artificial Sequence: Novel
      Sequence

<400> SEQUENCE: 5
ggugggcgcc gucggugugg gcaa                                                  24

<210> SEQ ID NO 6
<211> LENGTH: 19
<212> TYPE: RNA
<213> ORGANISM: Artificial Sequence
<220> FEATURE:
<223> OTHER INFORMATION: Description of Artificial Sequence: Novel
      Sequence

<400> SEQUENCE: 6
ggugggcaau gggcguguu                                                        19
```

```
<210> SEQ ID NO 7
<211> LENGTH: 19
<212> TYPE: RNA
<213> ORGANISM: Artificial Sequence
<220> FEATURE:
<223> OTHER INFORMATION: Description of Artificial Sequence: Novel
      Sequence

<400> SEQUENCE: 7
cuccaccaua guacacucc                                                      19

<210> SEQ ID NO 8
<211> LENGTH: 20
<212> TYPE: DNA
<213> ORGANISM: Artificial Sequence
<220> FEATURE:
<223> OTHER INFORMATION: Description of Artificial Sequence: Novel
      Sequence

<400> SEQUENCE: 8
tccgtcatcg ctcctcaggg                                                     20

<210> SEQ ID NO 9
<211> LENGTH: 20
<212> TYPE: DNA
<213> ORGANISM: Artificial Sequence
<220> FEATURE:
<223> OTHER INFORMATION: Description of Artificial Sequence: Novel
      Sequence

<400> SEQUENCE: 9
tcccgcctgt gacatgcatt                                                     20

<210> SEQ ID NO 10
<211> LENGTH: 20
<212> TYPE: DNA
<213> ORGANISM: Artificial Sequence
<220> FEATURE:
<223> OTHER INFORMATION: Description of Artificial Sequence: Novel
      Sequence

<400> SEQUENCE: 10
tctgagtagc agaggagctc                                                     20

<210> SEQ ID NO 11
<211> LENGTH: 20
<212> TYPE: DNA
<213> ORGANISM: Artificial Sequence
<220> FEATURE:
<223> OTHER INFORMATION: Description of Artificial Sequence: Novel
      Sequence

<400> SEQUENCE: 11
tccgtcatcg ctcctcaggg                                                     20
```

ZINC FINGER PEPTIDE CLEAVAGE OF NUCLEIC ACIDS

This application claims the benefit of U.S. Provisional Application No. 06/103,309, filed Oct. 6, 1998.

FIELD OF THE INVENTION

This invention is directed to certain peptides which have been found to cleave nucleic acid under controllable conditions. In accordance with certain preferred embodiments, members of the family of peptides, known as zinc finger peptides, have displayed the ability to cleave single stranded RNA. Diagnostic, therapeutic and research regimes are now possible featuring the cleavage function of such peptides and complexes comprising them.

BACKGROUND OF THE INVENTION

Zinc finger peptides comprise a class of protein which are known per se. See: Page, D. C., Mosher, R., Simpson, E., Fisher, E. M. C., Mardon, G., Pollack, J., McGillirray, B., de la Chapelle, A., and Brown, L. G. (1987) Cell 51, 1091–1104; and Weiss, M. A., and Keutmann, H. T. (1990) Biochemistry 29, 9808–9813. The entirety of each of the references cited in this specification is incorporated herein by reference. Such peptides, which are of moderate length, are known to include zinc as a coordinate ion, and are known to complex certain nucleic acids. It has previously been know that certain zinc finger peptides complex with certain nucleic acids. However, it has now been found that at least certain of such peptides, under controllable conditions, can have functions far different than heretofore suspected. Such new functionalities have been found to give rise to the use of zinc finger peptides and related molecules in therapeutics, in diagnostics and in research.

SUMMARY OF THE INVENTION

It has now been found quite surprisingly that, under controllable conditions, zinc finger peptides can selectively cleave nucleic acids. This observation is startling in view of the fact that such peptides are known to actually complex with nucleic acids. In particular, it has been found that when the zinc concentration attendant to a zinc finger peptide decreases, the peptide tends to homodimerize, forming a structure which cleaves nucleic acid, especially single stranded RNA.

For example, a 30 amino acid peptide has been identified from among the family of zinc finger peptides, which efficiently cleaves single strand RNA. The peptide sequence corresponds to a single zinc finger of the human male associated ZFY protein; a transcription factor belonging to the Cys2His2 family of zinc finger proteins. See the Mosher, Kochoyan and Weiss references, supra. The peptide:

HOOC-KTYQCQYCEY RSADSSNLKTHIKTKHSKEK-NH2 (SEQ ID No. 1) has been shown to give rise to RNA cleavage, but such cleavage was observed only in the general absence of zinc. It has been found that coordination of the peptide with zinc resulted in complete loss of ribonuclease activity. The kinetics of RNA cleavage for the zinc-free form of the finger peptide were comparable to rates observed for the Group II intron ribozymes, e.g., $V_O$, Kcat and Km of 6 nmol l-1 min-1, 0.96 s-1 and 105 nM, respectively). See Xiang, Q., Zhifeng Qin, P., Michels, W. J., Freeland, K., and Pyle, A. M. (1998) Biochemistry 37, 3839–3849.

The foregoing peptide appear to specifically cleave pyrimidines and preferentially cleave 5'-pyr-A-3' within single stranded RNA. RNA sequences containing 5'-pyr-A-3' were cleaved 10–30 fold faster than were those without such pyrimidine. The RNA cleavage products included a 3'-phosphate and 5'-hydroxyl. Single strand DNA, double strand RNA and DNA, and 2'-methoxy modified sequences were not hydrolyzed by this member of the class of zinc finger peptides, thus demonstrating selectivity. Divalent cations, (e.g., Mg2+ and Mn2+) were shown not to be required for catalysis. The pH for RNA cleavage with this peptide was pH 7.0. The bell shaped pH profile exhibited by the peptide is characteristic of general acid-base catalytic mechanisms observed with ribonucleases. Herries, D. G., Mathias, A. P., Rabin, B. R. (1962) Biochem. J. 85, 127; Del Rosario, E. J., Hammes, G. G. (1969) Biochemistry 8, 1884; Blackburn, P., and Moore, S. (1982) in The Enzymes (P. D. Boyer, ed.) 3rd ED. Vol. 15, pp435–468. Academic Press. N. Y.

Other zinc finger peptides, especially peptide mutants, are believed to exhibit the nucleic acid cleaving properties. Mutants to the peptide of Seq. I.D. No. 1 were synthesized in which Ala was substituted for His (H21,26A) and Glu (E9A). These mutants exhibited a 3–8 fold reduction in the cleavage rate but did not result in complete ablation in activity. This suggests a catalytic mechanism other than the one proposed for RNases A and T1. Blackburn, P., and Moore, S. (1982) in The Enzymes (P. D. Boyer, ed.) 3rd ED. Vol. 15, pp435–468. Academic Press. N.Y.; Takahashi, K and Moore, S. (1982) in *The Enzymes* (P. D. Boyer, ed.) 3rd ED. Vol. 15, pp435–468. Academic Press. N. Y.; and Roberts, G. C. K., Dennis, E. A., Meadows, D. H., Cohen, J. S., and Jardetzky, O. (1969) Proc. Natl. Acad. Sci. U.S.A. 62, 1151–1158.

Complete loss in ribonuclease activity was observed with Ala substitution of Lys residues (K19,20,23,25,28,30A) within the basic carboxyl terminal half of the peptide. These data suggest that positively charged basic region of the peptide may likely be binding electrostatically to the substrate. Polyacrylamide gel electrophoresis and mass spectral analysis indicated that the molecular weight of the peptide was consistent with peptide dimerization. The lack of dimer formation observed with the C5,8A peptide mutant suggest that peptide dimerization is via intermolecular disulfide bonds. Both monomer forms of the peptide, (e.g., C5,8A mutant and the reduced wild type peptide), exhibited no ribonuclease activity. Ribonuclease activity of the monomer form was regained with the substitution of Arg for Lys (K19,20,23,25,28,30R) suggesting that dimerization likely serves to enhance the binding of the peptide to the substrate but is not required for catalysis.

The ability of the zinc finger peptides to cleave nucleic acid, especially single stranded RNA, gives rise to their utility as therapeutics, diagnostics and research reagents. The destruction or disablement of RNA can be a useful event in interfering with disease states, as is well known to persons of skill in the art. Moreover, the ability to cleave single stranded RNA, especially selectively with respect to other nucleic acids and selectively with respect to situs of cleavage makes these molecules useful for research where such selective cleavage can readily be employed to advantage. Similarly, diagnosis of disease may be had through employment of zinc finger peptides to cleave RNA in a predictable fashion. These uses are particularly enhanced due to the fact that the activity is zinc dependent. Thus, by control, especially automated control, of zinc ion concentration, control of the cleavage reactions can be had. It will be appreciated that the zinc ion concentration is related to homodimer formation in the peptides. Thus, zinc ion formation and homodimer formation are related phenomena such that either or both can be used to monitor cleavage activity.

The zinc finger peptides useful in the practice of this invention are any of the family of such peptides together with mutants thereof which retain the ability to cleave nucleic acid under some controllable conditions such as zinc ion concentration. Mutants which improve specificity, reaction rate, or control functions are particularly preferred. While homodimer formation is a presently preferred interim assemblage preparatory to cleavage activity, such is not necessarily the case in some embodiments.

The ability of zinc finger peptides to selectively and controllably cleave nucleic acid, especially RNA make possible the preparation of zinc finger peptide complexes with particular activity. The covalent attachment of a zinc finger peptide to a targeting moiety, which can localize the peptide to a nucleic acid, such as an mRNA, whose cleavage or inactivation is desired, may be attained. Such attachment may be either directly, such that the peptide is directly bonded to such targeting moiety, or indirectly, whereby the peptide and targeting moiety are connected by a tether. In either case, the targeting moiety may be seen to localize the complex on or near a preselected nucleic acid, such as an mRNA important to disease. Such localization permits a high fidelity and rate of cleavage of the preselected RNA by the peptide.

Targeting moieties may be any molecule which binds specifically with a preselected nucleic acid labile to the zinc finger peptide. Oligonucleotides, such as antisense oligonucleotides are greatly preferred since they are known, are faithful in their specific binding, they can easily be synthesized and they are useful in drug, diagnostic and research formulations. Other targeting species such as small molecules, peptides, organometallics and the like may also be used.

The targeting moiety is bonded to the peptide in any convenient way such as through formation of an amide bond at the terminal carboxyl of the peptide, via a side chain function, through reaction at the terminal amine function or otherwise. Such reactions may either be directly with the targeting moiety or with a tether attached or to be attached thereto.

Tethers can be any molecule capable of bonding with both a targeting molecule or moiety and with a zinc finger peptide. Polyfunctional molecules are preferred as will be seen.

In use, zinc finger peptides of this invention are caused to contact a nucleic acid to be cleaved, especially an RNA. Preferably, the zinc concentration is reduced such that at least about 50 mole percent of the peptide is uncomplexed. Homodimer formation is believed to ensue with attendant, controlled cleavage. This mechanism may either directly cleave an RNA, such as a messenger RNA implicated in disease, thus diminishing the effects of the disease or can be used for diagnostics. Moreover, the phenomenon can be used in research where nucleic acid cleavage is widely used.

The zinc ion dependence of the activity is especially useful, since the activity can, in effect, be switched on and off and, indeed, potentiated.

Figure 1A:
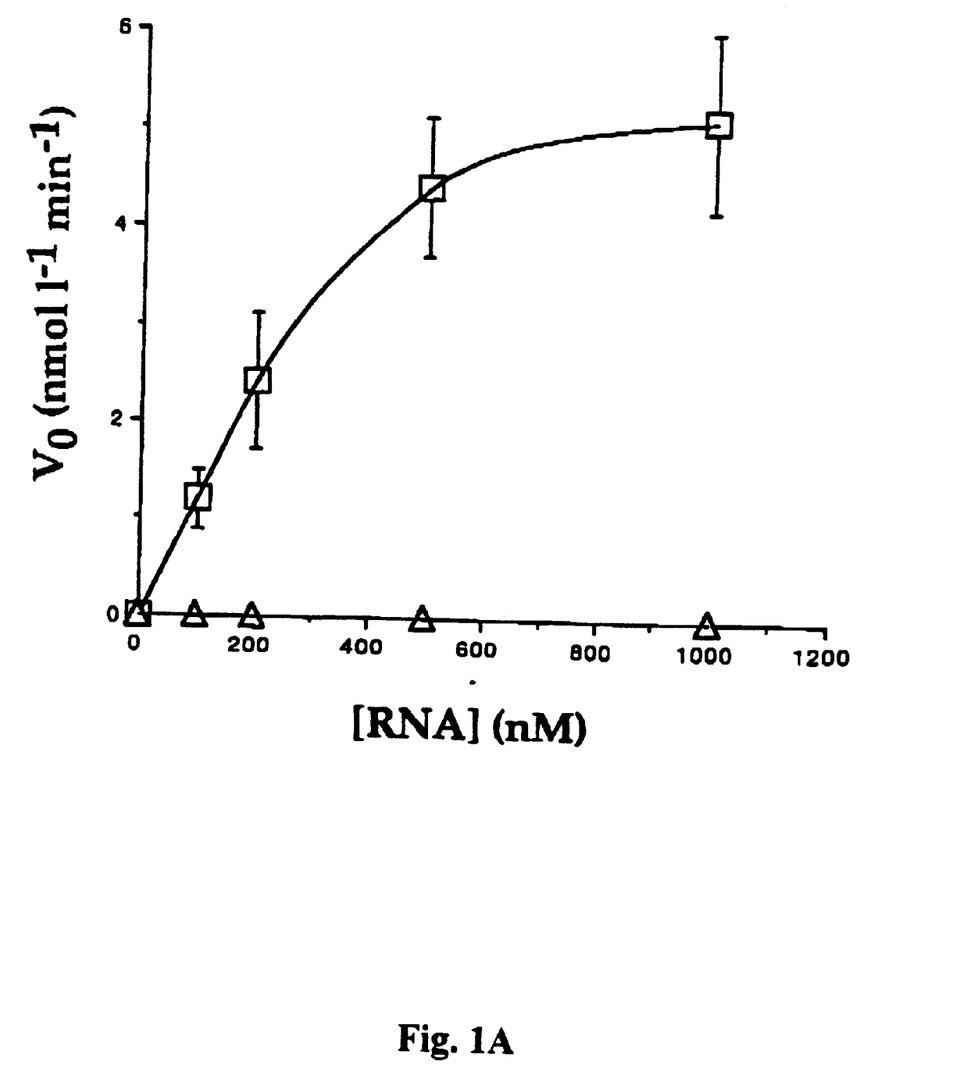
FIG. 1A depicts the kinetics of RNA cleavage by the finger peptide of SEQ. ID. NO.: 1.
Figure 1B:
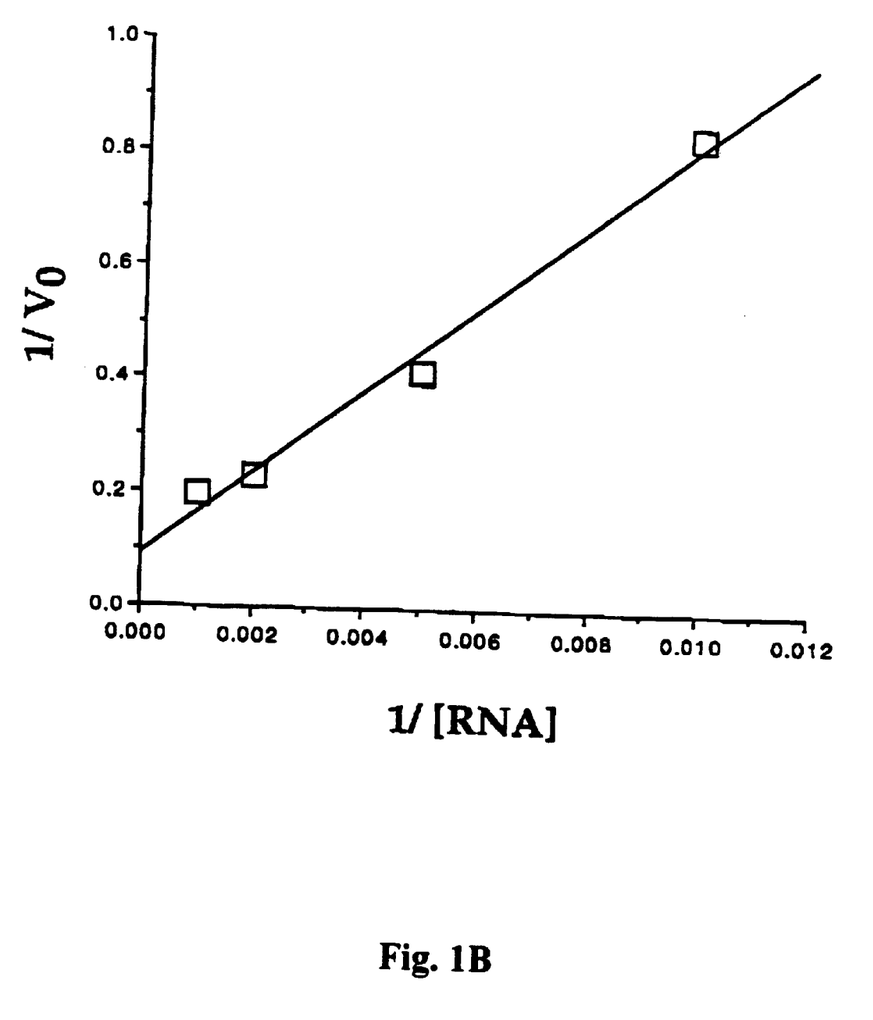
FIG. 1B depicts Lineweaver-Burk analysis of multiple turnover kinetics for the wild-type peptide of SEQ. ID NO.: 1.
Figure 1C:
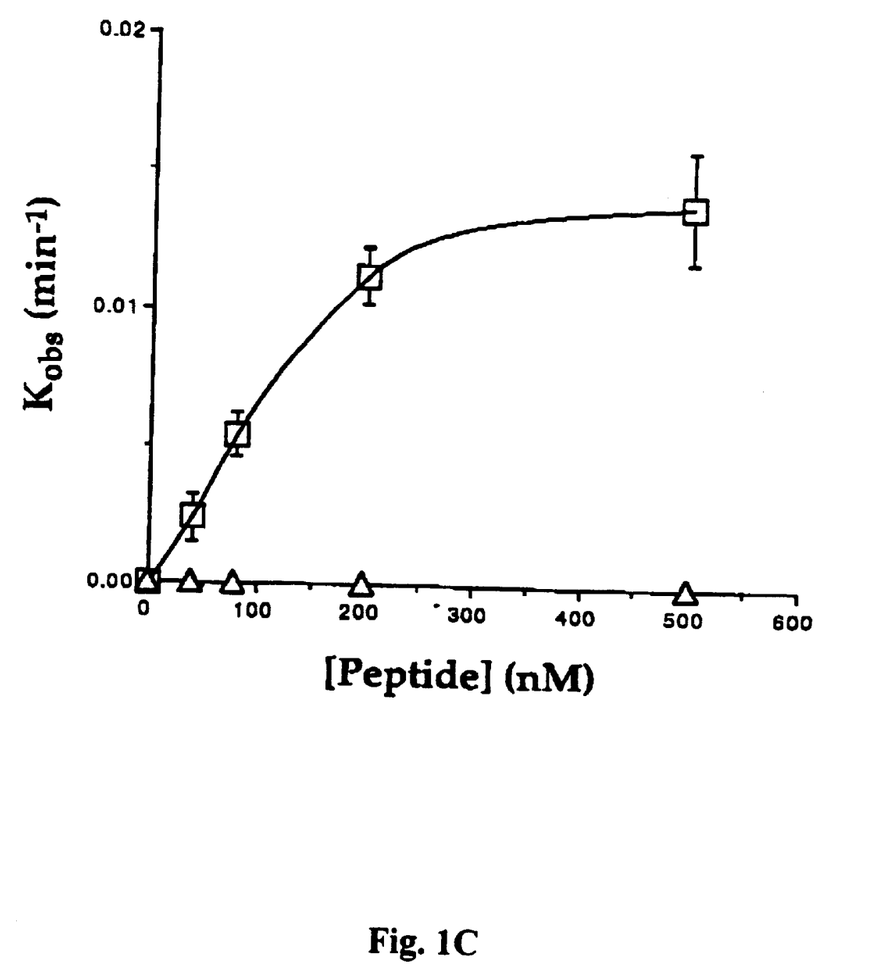
FIG. 1C depicts single turnover kinetics for the wild-type peptide (open box) and the wild-type peptide coordinated with zinc (open triangle).

FIG. 1A depicts the Kinetics of RNA Cleavage by the Finger Peptide of Seq. I.D. No. 1. Multiple turnover kinetics are shown for RNA cleavage by the wild-type peptide (open box) and wild-type peptide coordinated with zinc (open triangle). FIG. 1B shows Lineweaver—Burk analysis of multiple turnover kinetics for the wild-type peptide of Seq. I.D. No. 1. Multiple turnover kinetics were performed in 100 $\mu$L containing 50 nM peptide, 100 to 1000 nM or a 20—mer RNA oligonucleotide denominated 9713 and having Seq. I.D. No. 7, as 105 CPM 32P labeled RNA in 20 mM Sodium Phosphate, pH 7.0, 100 mM KCl, 1 mM EDTA, and 0.1% NP40. Digestion reaction were incubated at 37° C. and quenched at specific time points in 6 M urea. Digestion products were analyzed by denaturing polyacrylamide gel electrophoresis. FIG. 1C shows single turnover kinetics for the wild-type peptide (open box) and the wild-type peptide coordinated with zinc (open triangle). Single turnover kinetics were performed as described above with the exception that peptide ranging in concentration from 50 to 500 nM was added to 50 nM of the 9713 RNA, Seq. I.D. No. 7.

Table 1 shows cleavage specificity of the finger peptide. Initial rates of cleavage of several single stranded oligonucleotides were determined as described in connection with FIG. 1 with the exception that 50 nM wild-type peptide and 500 nM oligonucleotide were used. Arrows indicate the position of the peptide induced cleavage. The relative intensity of the cleavage product for each respective cleavage sites is indicated by the length of the arrows.

TABLE 1

| SUBSTRATE | SEQ ID | $V_0$ pmol$^{-1}$ min$^{-1}$ | SEQUENCE |
|---|---|---|---|
| 4701 (DNA) | 2 | 0 | CUCCACCAUAGUACACUCC |
| 12079 (2'-OMe) | 3 | 0 | ACUCCACCAUAGUACACUCC |

TABLE 1-continued

| SUBSTRATE | SEQ ID | $V_0$ pmol$^{-1}$ min$^{-1}$ | SEQUENCE |
|---|---|---|---|
| 3058 (RNA) | 4 | 153 |  GGCGCCGUCGGUGUGG |
| 2755 (RNA) | 5 | 422 |  GGUGGGCGCCGUCGGUGUGGGCAA |
| 12147 (RNA) | 6 | 1200 |  GGUGGGCAAUGGGCGUGUU |
| 9713 (RNA) | 7 | 6100 |  CUCCACCAUAGUACACUCC |

Figure 2:
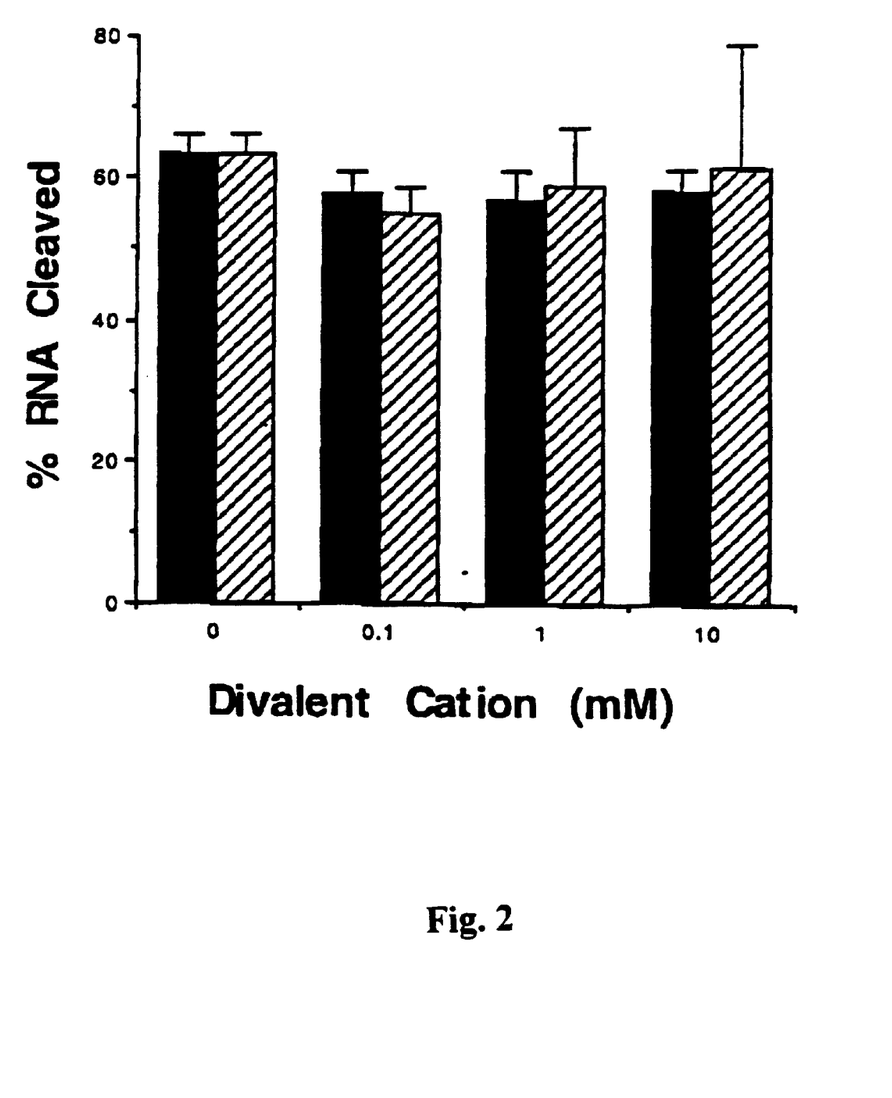
FIG. 2 depicts the effect of divalent cations on the RNA cleavage activity of a zinc finger peptide of SEQ. ID NO: 1.

FIG. 2 shows the effect of divalent cations on the RNA cleavage activity of a zinc finger peptide of Seq. I.D. No. 1. Digestion reactions were performed as described in FIG. 1 in the presence of either Mg2+ (solid) or Mn2+ (hashed). Reactions were quenched at 30 min. and digestion products analyzed by denaturing polyacrylamide gel electrophoresis.

Figure 3A:
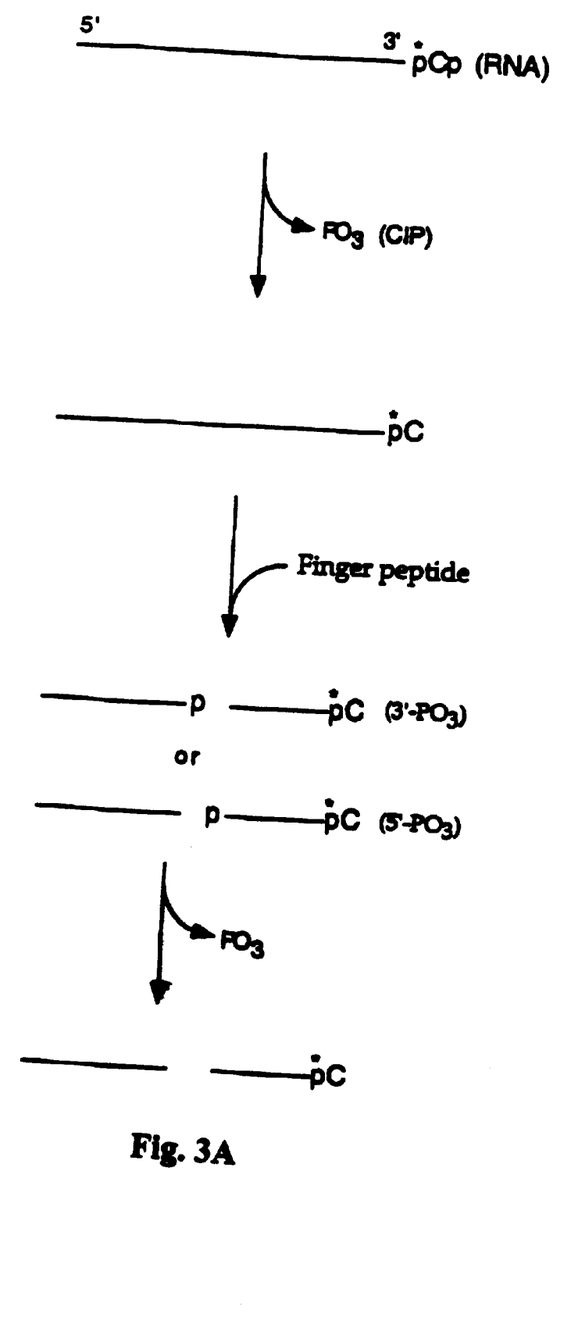
FIG. 3A depicts a schematic cleavage product analysis of RNA substrate.
Figure 3B:
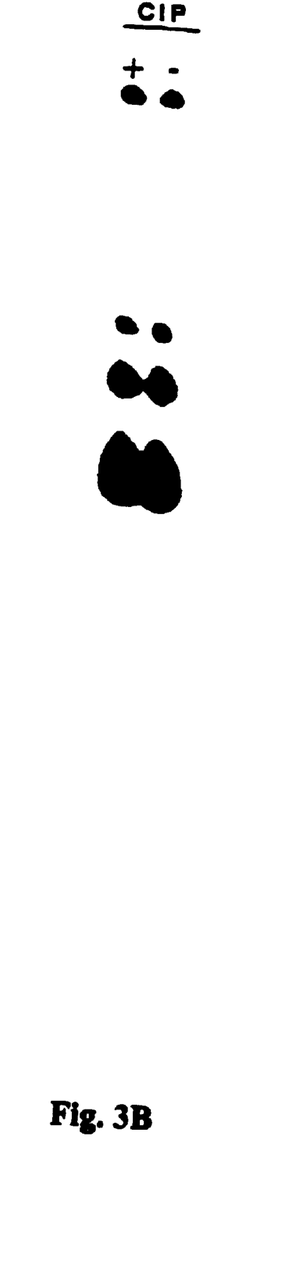
FIG. 3B depicts comigration of both the Lintreated and dephosphorylated aliquote.

FIG. 3A presents a schematic cleavage product analysis of RNA aubstrate. RNA substrate 9713, Seq. I.D. No. 7, was internally labeled at the penultimate 3' phosphate using ($^{32}$P) cytidine bisphosphate and T4 RNA ligase. The 3' terminal phosphate was removed using calf intestinal phosphatase and the RNA digested with the wild type peptide as described in the schematic of FIG. 3A. The digestion reactions were divided into equal aliquots and one aliquot subjected to an additional dephosphorylation. The digested products were analyzed by denaturing polyacrylamide gel electrophoresis. FIG. 3B shows comigration of both the untreated and dephosphorylated aliquote suggesting that the cleavage of the RNA by the peptide produces 3'-phosphate and 5'-hydroxyl termini.

Figure 4:
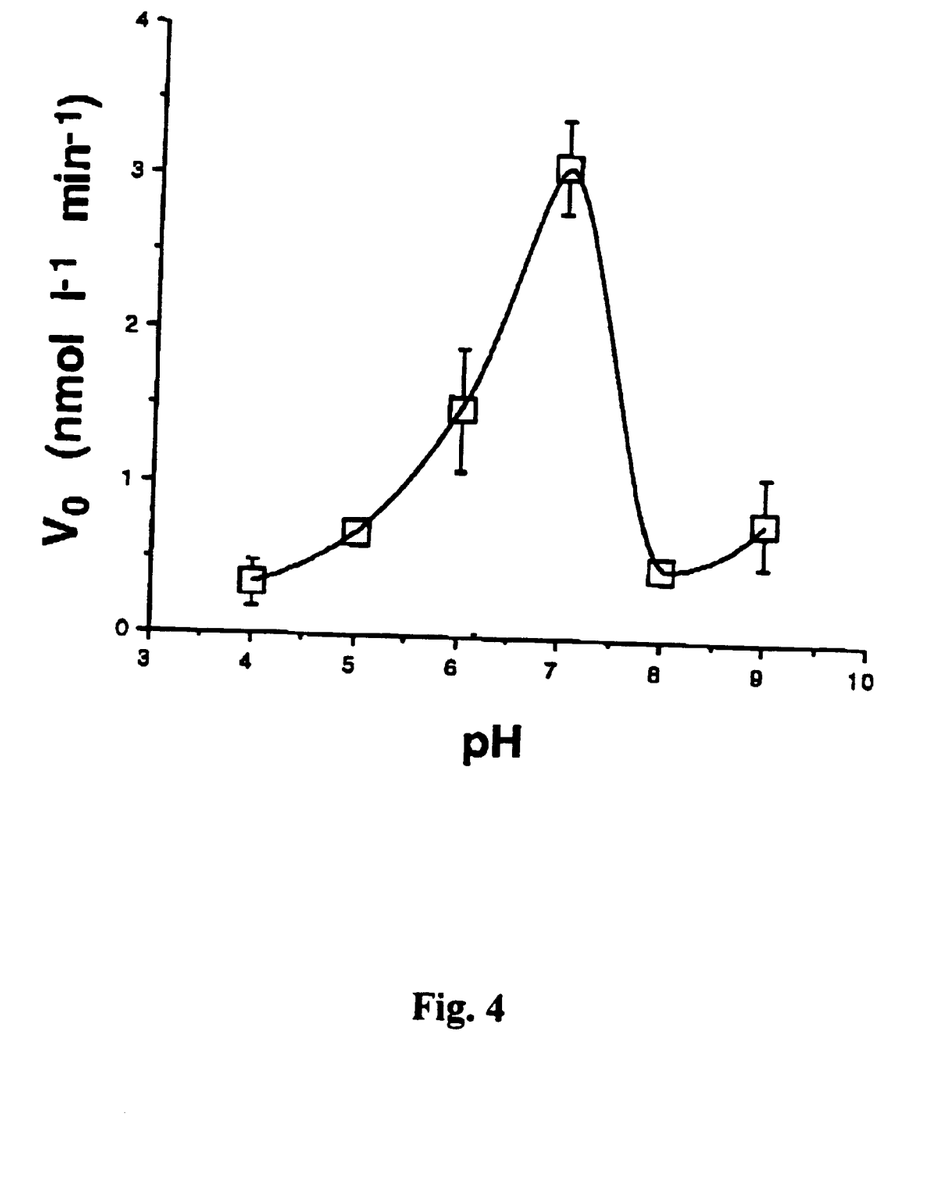
FIG. 4 depicts the pH dependence of RNA cleavage by the finger peptide of SEQ. ID NO. 1.

FIG. 4 shows The pH dependence of RNA cleavage by the finger peptide of Seq. I.D. No. 1. Initial rates were determined as described in connection with FIG. 2. For each rate determination the pH was adjusted using either 20 mM sodium acetate, pH 4, 20 mM sodium phosphate, pH 5 to pH 8 or 20 mM sodium carbonate, pH 9.

Table 2 shows the relationship between peptide structure and RNA cleavage activity for the wild type and mutant peptides. Initial rates were determined as described in connection with FIG. 2. Peptide structure was determined by SDS PAGE and LC-MS. Mass spectral analysis of the wild type peptide suggest dimerization of the peptide is via the formation of a single disulfide bond between two of the four available cysteines. The two remaining cysteines were reduced, exhibiting free sulfhydryl groups. Dimerization of the peptide appears to be required for RNA cleavage activity, i.e., no RNase activity was observed for the monomeric form of the peptide.

TABLE 2

| PEPTIDE | $V_0$ (9713) pmol$^{-1}$ min$^{-1}$ | PEPTIDE STRUCTURE |
|---|---|---|
| Wild type | 6000 ± 130 | Dimer |
| $E_9A$ | 1800 ± 90 | Dimer |
| $H_{21,26}A$ | 800 ± 30 | Dimer |
| $C_{5,8}A$ | 0 | Monomer |
| $C_{5,8}A/H_{21,26}A$ | 0 | Monomer |

Figure 5:
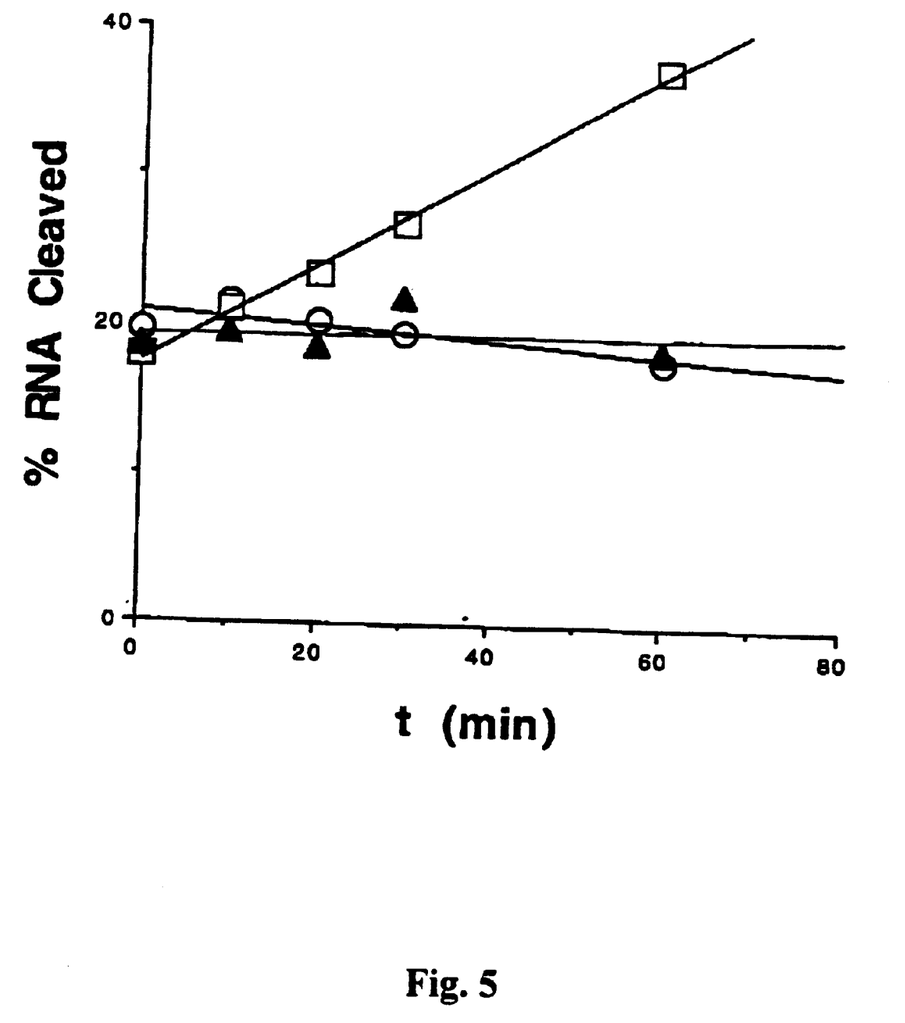
FIG. 5 depicts a comparison of the RNA cleavage activity for the dimeric and monomeric forms of the wild type peptide of SEQ. ID NO.: 1.

FIG. 5 presents a comparison of the RNA cleavage activity for the dimeric and monomeric forms of the wild type peptide Seq. I.D. No. 1. The RNA cleavage activity for the monomeric (solid triangle) and dimeric (open box) forms of the wild type peptide were compared with the $C_{5,8}A$ peptide mutant (open circle). No cleavage of the RNA was observed for either the wild type monomer or $C_{5,8}A$ monomer peptides, suggesting that only the dimeric form of the wild type peptide exhibits RNase activity. The wild type monomer peptide was prepared in 1 mL containing 1 to 5 mM peptide, 200 mM DTT and 6 M Urea and incubated for 2 h at 60° C. The reduced peptide was purified under acidic conditions (pH 2) by reverse phase chromatography. The RNA cleavage activity for the peptides were determined as described in connection with FIG. 2 with the exception that peptides were preincubated with the RNA at pH 4 for 30 min. and adjusted to pH 7 with 20 mM sodium carbonate, pH 9, for the digestion reaction.

Figure 6:
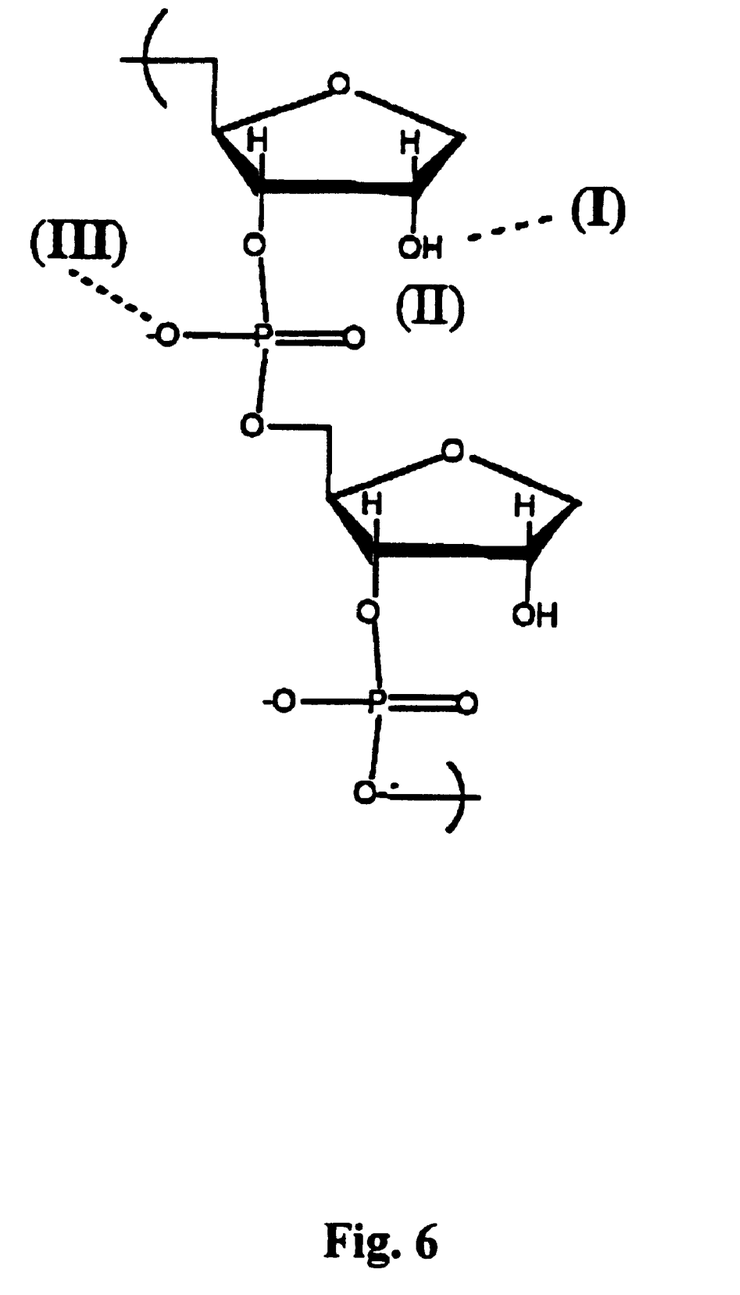
FIG. 6 depicts a proposed a cleavage mechanism.

FIG. 6 proposes a cleavage mechanism, with the understanding that the applicants do not choose to be bound by theory. The schematic illustrates a cleavage mechanism involving a metal independent, amino acid induced general acid-base hydrolysis of the RNA by the peptide. The classic description of this mechanism involves the deprotonation of the 2'-hydroxyl by the peptide (I), nucleophilic attack of the phosphorous center by the 2'-oxygen (II) resulting the formation of a 2',3'-cyclic phosphate intermediate and subsequent hydrolysis of the phosphate ester accompanied by protonation of the leaving oxygen by the peptide (III). Evidence for this catalytic model is based on the following observations

First, cleavage of the RNA by the peptide involves a metal independent mechanism similar to that observed for other single strand ribonucleases which have been shown to hydrolyze RNA via amino acids residues from the enzyme. Blackburn, P., and Moore, S. (1982) in The Enzymes (P. D. Boyer, ed.) 3rd ED. Vol. 15, pp435–468. Academic Press. N. Y; Takahashi, K and Moore, S. (1982) in The Enzymes (P. D. Boyer, ed.) 3rd ED. Vol. 15, pp435–468. Academic Press. N. Y.; and Roberts, G. C. K., Dennis, E. A., Meadows, D. H., Cohen, J. S., and Jardetzky, O. (1969) Proc. Natl. Acad. Sci. U.S.A. 62, 1151–1158. Moreover, the bell-shaped pH vs. rate profile is consistent with a general acid-base catalytic mechanism; Heries, Del Rosario and Blackburn, supra.

DNA and 2'-methoxy modified sequences were not degraded by the peptide suggesting that the 2'-hydroxyl is required for cleavage. Under the proposed cleavage mechanism and consistent with the observed peptide induced RNA cleavage products, hydrolysis of the RNA would result in digestion products consisting of 5'-hydroxyl and 3'-phosphate termini. Roberts, G. C. K., Dennis, E. A., Meadows, D. H., Cohen, J. S., and Jardetzky, O. (1969) Proc. Natl. Acad. Sci. U.S.A. 62, 1151–1158; and Ikehara, M., Ohtsuka, E., Togunaga, T., Nishikawa, S., Uesugi, S., Tanaka, T., Aoyana, Y., Kikyodani, S., Fugimoto, K., Yanase, K., Fuchimura, K., and Morioka, H. (1986) Proc. Natl. Acad. Sci. U.S.A. 83, 4695.

The initial cleavage rate (V0) for the peptide is comparable with other ribonucleases which are predicted to participate in both proton abstraction and donation and significantly faster than rates observed for RNA cleavage by proton abstraction alone. Haner, R., and Hall, J. (1997) Antisense and Nucleic Acid Drug Development 7, 423–430; Tung, C-H., Wei, Z., Leibowitz, M. J., and Stein, S. (1997) Proc. Natl. Acad. Sci. U.S.A. 89,7114–7118; and Barbier, B., and Brack, A. (1992)J. Am. Chem. Soc. 114,3511–3515.

Conjugating Zn-finger peptide of transcription factor, "ZFY" to an oligonucleotide may be accomplished in a number of ways. One convenient way is via the amino terminus. Usually a cys amino acid is added to the peptide at the amino terminus for conjugation purposes to yield either a disulfide linkage or a thioether linkage. The reaction occurs via the —SH group. However, most Zn finger peptides already have two cys units in their middle; these may be needed in the cleavage activity. It can be difficult to distinguish among these cys groups for conjugation purposes (linker cys vs. functional cys groups). The same is true in using lys as a tether for conjugation. The peptide has several lysines and use of these lys functionalities for conjugation is not advisable as they may be needed for either binding or cleavage activity. If a lysine tether is added, one cannot then distinguish chemically the tethered lysine from the internal lysine functions.

At least three different, novel conjugation approaches have been developed to deal with these difficulties. First, this may be accomplished by introduction of an —O—NH$_2$ tether in the targeting oligonucleotide and conjugating that function to an aldehyde group present in a tether on the peptide. Alternatively, there may be introduction of an aldehyde tether in oligonucleotides and a —ONH$_2$ tether in the peptides. Moreover, one may employ introduction of two olefinic tethers, one in the peptide and one in oligonucleotide followed by a Grubbs olefin metathesis cross-coupling or similar reaction. These can be seen schematically:

The present invention is easily amenable to therapeutics, diagnostics and for research. Since the zinc concentration directly and dramatically effects dimerization and concomitant cleavage of nucleic acid, such cleavage may be accomplished under conditions of great control. Automated equipment, through zinc ion manipulation, may effect nucleic acid cleavage in a routine and repetitive fashion. The same is useful for automated sequencing, synthesis and the like. Wide application in research and diagnostics may be attained.

Such use is particularly advantageous since tethering such peptides to an oligomeric or small molecule specificity enhancing moiety can lead to highly specific cleavage of nucleic acids, specific not only as to situs, occurring at the pyrimidines, but also as to molecular identity. Thus, e.g., cleavage of specific RNAs can be attained hereby.

Such specificity gives rise to employment in pharmaceuticals. oligomer-tethered zinc finger peptides can cleave specific RNA—s in animals. When such RNAs are those implicated in disease states, therapeutic benefit is attained. This is especially so where the oligomer is specifically hybridizable with the target RNA.

The invention is further illustrated by reference to the following non-limiting examples.

OLEFINIC AND ALDEHYDE TETHERS IN THE PEPTIDE

Example 1
Pentafluorophenyl ester of 4-pentenoic acid 4-pentenoic acid (Aldrich) is treated with pentafluorophenol and N,N-dicyclo hexylcarbodiimide (DCC) (1 equivalent each) in dioxane solvent and stirred overnight. The resulting N-N-dicyclohexyl urea (DCU) is filtered off and the solid residue is washed with methylene chloride ($CH_2Cl_2$). The combined solution is evaporated and the resultant ester is purified in a silica gel chromatographic column.

Example 2
Coupling of olefinic group at the amino terminal of the Zn-finger peptide The 30 mer Zn-finger peptide is built using standard peptide synthesis protocol. The final amino residue is deprotected and coupled with pentafluorophenyl ester of 4-pentenoic acid. This gives an olefinic double bond functionality at the amino terminus of the peptide. This peptide with the olefin tether is then cleaved from the resin and purified. The peptide is characterized by mass spectral and amino acid analysis.

OLIGONUCLEOTIDES WITH OLEFINIC AND ALDEHYDE TETHERS

Example 3
Cytidine and thymidine nucleosides with a 2'-O-(4-penten-1-yl) residues 4-penten-1-ol (50 mmol) is slowly added to a solution of borane in tetrahydrofuran (1 M, 10 mL, 10 mmol) with stirring in a 100 mL bomb. Hydrogen gas evolved as the reagent dissolved. O-2, 2'-anhydro-5-methyluridine (1.2 g, 5 mmol) and sodium bicarbonate (25 mg) were added and the bomb is sealed, placed in an oil bath and heated to 155° C. for 36 hrs. The bomb is cooled to room temperature and opened. The crude solution is concentrated and the residue partitioned between water (200 mL) and hexanes (200 mL). The excess olefinic alcohol is extracted into hexanes. The combined organic layer is concentrated and purified by silica gel flash column chromatography using methanol:methylene chloride (1/10, v/v) as the eluent. Fractions are collected and the target fractions are concentrated to give 2'-O—(4-penten-1-yl)-5-methyluridine. This compound is treated with 1–2 equivalents of dimethoxytrityl chloride (DMT-cl) in pyridine to yield 5'-dimthoxytrityl-2'-O—(4-penten-1-yl)-5-methyluridine which is subsequently purified in a silica gel column.

Example 4
5'-O-Dimethoxytrityl-2'-O-(4-penten-1-yl)-5-methyluridine-3'-O-cyanoethyl-N,N-diisopropylamino)phosphoramidite The 5'-protected-2'-modified nucleoside from the previous step is phosphitylated under argon atmosphere using N,N-diisopropylaminohydrotetrazolide (0.5 equivalents) and bis-N,N-diisopropylamino-2-cyanoethyl-phosphoramidite (2 equivalents) in anhydrous $CH_2Cl_2$ solvent. The product is purified by silica gel column.

Example 5
5'-O-dimethosytrityl-2'-O-(4-penten-1-yl)-5-methyluridine-3'-O-succinyl-amido-controlled pore glass The 5'-protected nucleoside from Example 3 is treated with 2 equivalents of succinic anhydride and 0.2 equivalents of 4-N,N-dimethylaminopyridine in pyridine solvent. After 2 hours the pyridine is evaporated. The residue is dissolved in $CH_2Cl_2$ and washed three times with 100 mL of 10% citric acid solution. The organic layer is dried over anhydrous $MgSO_4$ to give the desired succinate. The succinate is then attached to controlled pore glass (CPG) using established procedures (Manoharan et al., Tetrahedron Lett. 36, 3647, 1995).

Example 6
3'-O-acetyl-2'-O-(4-penten-1-yl)-5'-O-dimethoxytrityl-5-methyluridine Nucleoside from Example 3 is dissolved in chloroform. To this is added 4-N,N-1-dimethylaminopyridine followed by acetic anhydride and the reaction mixture is stirred overnight. Aqueous work-up followed by silica column purification yielded the title compound.

Example 7
2'-O-(4-penten-1-yl)-5-O-dimethoxytrityl-N4-benzoyl-5-methylcytidine A suspension of 1,2,4-triazole (4 equivalents) in anhydrous $CH_3CN$ is cooled in an ice bath for 5 to 10 min under argon atmosphere. To this cold suspension $POCl_3$ (1 equivalent) is slowly added over 10 min and stirring continued for additional 5 min. Triethylamine (5 equivalents) is added slowly over 30 min keeping the bath temperature around 0° C. After the addition is complete, the reaction mixture is stirred at this temperature for an additional 30 min, at which point the nucleoside from Example (0.25 equivalent) is added in anhydrous $CH_3CN$ and the mixture is stirred for 10 min at 0° C. and then at room temperature for 1.5 hr. The reaction mixture is concentrated, extracted with ethylacetate and dried over anhydrous $Na_2SO_4$. The resulting solution was concentrated and dissolved in saturated solution of ammonia in dioxane and stirred at room temperature overnight. Solvent is removed under vacuum. The residue is purified by silica gel column chromatography.

This cytidine derivative is then dissolved in anhydrous DMF and treated with benzoic anhydride (1.5 equivalents to 1 equivalent for nucleoside). Methanol is added and solvent evaporated to dryness. Residue is dissolved in $CH_2Cl_2$ and washed with saturated solution of $NaHCO_3$ followed by brine. $CH_2Cl_2$ layer is dried over anhydrous $Na_2SO_4$ and concentrated. The residue obtained is purified by silica gel chromatography and eluted with 5% $CH_3OH$ in $CH_2Cl_2$ to yield the desired product.

Example 8
5'-O-dimethoxytrityl-2'-O-(4-penten-1-yl) N4-benzoyl-5-methylcytidine-3'-phosphoramidite Phosphoramide synthesis is achieved following the protocol described under the Example 4 and starting with the nucleoside from the previous step.

Example 9
5'-O-dimethoxytrityl-2'-O-(4-penten-1-yl) N4-benzoyl 3O-succinylamide-CPG The 5-methyl-cytidine from Example is converted to the nucleoside-CPG following the procedure described for the 5-methyl-uridine derivative.

Example 10
General Procedure for Oligonucleotide Synthesis

The olfinic tether containing amidite compound (0.39 mmol) is dissolved in 3.9 mL of anhydrous acetonitrile and loaded onto an Expedite Nucleic Acid Synthesis system (Millipore 8909) to synthesize oligonucleotides. The concentration of amidites is 0.1 M. The coupling efficiencies are optimized to be more than 95%. For the coupling of the novel amidite the coupling time is extended to 10 min. and this step is carried out twice. All other steps in the protocol supplied by Millipore are used as such. The oligomers are cleaved from the controlled pore glass (CPG) supports and deprotected under standard conditions using concentrated aqueous NH$_4$OH (30%) at 55° C. 5'-O-DMT-containing oligomers are then purified by reverse phase high performance liquid chromatography (C-4 column, Waters, 7.8× 300 mm, A=50 mM triethylammonium acetate, pH=7, B=acetonitrile, 5–60% of B in 60 min., flow 1.5 mL/min.). Detritylation with aqueous 80% acetic acid and evaporation, followed by desalting in a Sephadex G-25 column gave modified oligonucleotides. Oligonucleotides were analyzed by HPLC, CGE and mass spectrometry.

waxy solid (yield 93%). 13C NMR: d 21.94, 24.83, 27.58, 33.26, 78.26, 114.91, 123.41, 128.40, 128.54, 128.63, 134.45 and 163.8 ppm.

Example 13
N-(1-hydroxyphthalimido-5,6-hexane-diol)

N-(1-hydroxyphthalimido)-5-hexane (2.59 g, 10 mmol), aqueous osmium tetroxide (0.15 M, 3.6 mL, 0.056 mmol) and N-methylmorpholine-N-oxide (2.46 g, 21 mmol) were dissolved in THF (100 mL). The reaction mixture was covered with aluminum foil and stirred at 25° C. for 4 hours. TLC indicated the diol was formed. The solvent was evaporated and the residue was partitioned between water and CH$_2$Cl$_2$. The organic layer was washed with a saturated solution of NaCl and dried over anhydrous MgSO$_4$. Concentration of the organic layer resulted in a brownish oil that was characterized by $^{13}$C NMR and used in the next step without further purification. $^{13}$C NMR: d 21.92, 28.08, 32.62, 66.76, 71.96, 78.33, 123.43, 128.47, 128.71, 131.93, 132.13, 134.49, 163.89.

Example 14
N-1-hydroxy phthalimido-6-O-dimethyoxytrityl-5,6 hexane-diol

The product from the previous step (3.0 g) was coevaporated with pyridine (2×20 mL) and dissolved in pyridine (100 mL). Dimethoxytrityl chloride (3.5 g, 10 mmol) was

OLIGONUCLEOTIDES

| Seq. I.D. | Sequence (5'–3') asterisk | (All nucleosides with an contain olefinic tether) | Backbone | Chemistry | Target |
|---|---|---|---|---|---|
| 8 | T*CC GTC ATC GCT CCT CAG GG | | P = S | 2'-H | Ha-ras |
| 9 | TCC CGC CTG TGACATGCA TT* | | P = S | 2'-H | C-raf |

Example 11
Ligation of Oligonucleotide to Peptide via Olefin Metathesis Reaction Oligonucleotide with the 3'-terminal olefin group is mixed with peptide with olefinic linker and mixed with Grubbs catalyst (cy3P) Cl Ru: CHCH:CPh$_2$ (cy=cyclohexyl) to allow the metathesis between the olefinic linkages. The oligonucleotide-peptide conjugate is separated from other side products using anion-exchange HPLC methodology. (Grubbs, R. H.; Chang, S. "Recent advances in olefin Metathesis and Its Application in Organic Synthesis"; Tetrahedron, 54, 4413–4450, 1998.)

Example 12
Oligonucleotides with —O—NH$_2$ linker ("O—N linker") N-(1-hydroxyphthalimido)-5-hexene To a stirred solution of 5-hexane-1-ol (20 g, 0.2 mol) in THF (500 mL) was added triphenylphosphine (80 g, 0.3 mol) and N-hydroxyphthalimide (49 g, 0.3 mol). The mixture was cooled to 0° C. and diethylazido carboxylate (48 mL, 0.3 mol) was added slowly over a period of 1 hour. The reaction mixture was allowed to warm to room temperature and the yellow solution was stirred overnight. The solvent was then evaporated to give a yellow oil. The oil was dissolved in CH$_2$Cl$_2$ and washed with water, saturated NaHCO$_3$ solution followed by a saturated NaCl solution. The organic layer was concentrated in vacuo and the resulting oil was dissolved in a solution of CH$_2$Cl$_2$/ether to crystallize out Ph$_3$P=O as much as possible. After three steps of purification the title compound was isolated as a yellow dissolved in of pyridine (30 mL) and added to the diol dropwise over a period of 30 minutes. After 4 hours, the reaction was quenched with methanol (10 mL). The solvent was evaporated and the residual product portioned between saturated sodium bicarbonate solution and CH$_2$Cl$_2$ (100 mL each). The organic phase was dried over anhydrous MgSO$_4$, concentrated and the residue was subjected to silica gel flash column chromatography using hexanes-ethyl acetatetriethyl amine (60:39:1). The product containing fractions were combined, concentrated in vacuo and dried to give a yellow foamy solid. NMR analysis indicated the title compound as a pure homogenous dimethoxytritylated solid (5.05 g, 83% yield).

Example 15
O—N linker phosphoramidite

Compound from the previous step was phosphitylated (1.5 g, 2.5 mmol) in CH$_2$Cl$_2$ solvent (20 mL) by the addition of diisopropylamine tetrazolide (214 mg, 1.25 mmol) and 2-cyanoethyl-N,N,N,N -tetraisopropyl phosphorodiamidite (1.3 mL, 4.0 mmol). After stirring the solution overnight the solvent was evaporated and the residue was applied to silica column and eluted with hexanes-ethyl acetate-triethylamine (50:49:1). Concentration of the appropriate fractions gave 1.61 g of the phosphitylated compound as a yellow foam (81%).

Example 16
Attachment of O—N linker to CPG

Succinylated and capped CPG was prepared according to method described Damha et al., Nucleic Acids Res. 115, 7128 (1990). Compound containing the O—N linker (0.8 mmol), dimethylaminopyridine (0.2 mmol), 2.0 g of succinylated and capped CPG triethylamine (160 microL) and DEC (4.0 mmol) were shaken together for 24 hours. Pentachlorophenol (1.0 mmol) was then added and the resulting mixture was shaken for 24 hours. The CPG beads were filtered off and washed thoroughly with pyridine (30 mL) dichloromethane (2×30 mL), $CH_3OH$ (30 mL) in ether. The CPG solid support was dried over $P_2O_5$ and its loading was determined to be 28 micromols/g.

Example 17

Synthesis of oligonucleotides carrying O—N linker

The following oligonucleotides are synthesized using O—N linker "X":

| Seq.I.D.No 10 | 5' XTCT GAG TAG CAG AGG AGC TC 3' | | |
|---|---|---|---|
| Target: ICAM-1 | | 2'-MOE P = O | |
| Seq.I.D.No.11 | 5' TC | CGTCATCGCT | CCTCAGGG-X 3' |
| "Gap-mer" | 2'-MOE | 2'-H | 2'-MOE |
| Target: H-ras | P = S | P = S | P = S |

These oligonucleotides were synthesized either as phosphodiester (Seq. I.D. No. 10) or as a phosphorothioate (Seq. I.D. No. 11). For the synthesis of Seq. I.D. No. 10, the phosphoramidite compound is used as a 0.2 M solution in $CH_3CN$. The coupling efficiency of ON-linker is optimized to be >95% as can be evaluated by trityl colors. The oligonucleotides were deprotected from the solid support using concentrated ammonium hydroxide and this genrates the free —O—$NH_2$ linker for conjugation. Alternatively the oligomer is left in the solid support to carry out the conjugation in the solid support itself after generating the linker.

Example 18

Generation of Peptide Aldehyde from Peptides with Olefinic Tethers and Conjugation of Peptide to Oligonucleotide via an Oxime Linkage The peptides with olefinic tethers generated in Example 2 are ozonolyzed to yield aldehydes. Alternatively, the peptide with olefinic linker at the amino end is treated with $OsO_4$/NMMO followed by $NaIO_4$ This gives a free aldehyde tether at the amino end of the peptide. This peptide is treated with oligonucleotides containing O—N linker. —O—$NH_2$ group in the oligonucleotide is generated by $NH_4OH$ deprotection of the synthesized material in the previous step in solution or methylhydazine deprotction in solid support. After allowing the conjugation reaction to proceed to completion, the oxime-linked oligonucleotide is purified by anion-exchange resin.

Example 19

Conjugation of peptide to oligonucleotides using O—N-linker

Oligonucleotide having Sequence I.D. No. 10, with CPG (1 micromol) is taken in a glass funnel reactor and of 5% methylhydrazine (5 mL) in 9:1 $CH_2Cl_2$/$CH_3OH$ was added. The reactor is shaken for 10 minutes. The methyl hydrazine is drained, washed with $CH_2Cl_2$ and the methyl hydrazine reaction was repeated. The beads were washed with $CH_2Cl_2$ followed by ether and dried. Peptide with an aldehyde linker in DMF (5 mL) is added. After shaking for 2 hours, the peptide solution is drained; the oligonucleotide is deprotected in 0.1N NaOH overnight at room temperature. The aqueous solution is then filtered and an HPLC analysis is run. The conjugate product peak had a different retention time than the oligonucleotide and peptide precursors and the diode-array spectrophotometer showed the expected 260/280 absorption.

Example 20

Conjugation of peptide aldehyde to oligonucleotide (SEQ ID NO:11) in solution

Deprotection of CPG followed by $NH_4OH$ cleaving of CPG yielded oligonucleotide Seq. I.D. No. 1 in solution. Peptide aldehyde is added to the deprotected and purified oligonucleotide SEQ ID NO. 11 in solution. The conjugation is allowed to proceed and monitoed by reverse phase HPLC. The conjugate product peak had a different retention time than the oligonucleotide and peptide precursors and the diode-array spectrophotometer showed the expected 260/280 absorption.

Example 21

O-Aminolinker Attached Peptide 6-hydroxycaproic acid is treated with N-hydroxyphthalimide (2 equivalents) and diethyl azodicarboxylate (2 equivalents) at −78° C. is distilled THF solvent. The reaction mixture is warmed to ambient temperature and the solvent is evaporated in vacuo to give a solid residue. The solid residue is purified by silica gel column chromatography to give 6-phthalimidohydroxy-hexanoic acid-N-hydroxy-phthalic ester. This compound is coupled to the peptide at the amino terminal. The O—N linker is generated by treating the peptide with 5% methylhydrazine in methylene chloride.

Example 22

Conjugation of Peptide with O—N Linker to Oligonucleotide with Aldehyde Tether.

The oligonucleotide with olefinic linker is taken in water and treated with $OsO_4$/NMMO followed by $NaIO_4$. This gives a free aldehyde tether at the tether of the oligonucleotide. This oligonucleotide is then treated with peptide containing O—N linker from the previous step. After allowing the conjugation reaction to proceed to completion, the oxime-linked oligonucleotide is purified by anion-exchange resin. The conjugate product peak had a different retention time than the oligonucleotide and peptide precursors and the diode-array spectrophotometer showed the expected 260/280 absorption.

What is claimed is:

1. A method for selectively cleaving single stranded RNA comprising: contacting said single stranded RNA with a zinc finger peptide in the absence of zinc, wherein said dimerized zinc finger peptide comprises SEQ ID No. 1.

2. The method of claim 1 wherein said zinc finger peptide is not complexed with divalent metals.

3. The method of claim 1 wherein said contacting is under conditions selected to promote the dimerization of said peptide.

4. A chemical reagent comprising a dimerized zinc finger peptide, wherein said dimerized zinc finger peptide comprises SEQ ID No. 1.

5. A zinc finger peptide complex comprising a zinc finger peptide tethered to an oligonucleotide, wherein said zinc finger peptide comprises SEQ ID No. 1.

6. The complex of claim 5 wherein the oligonucleotide has a preselected sequence.

7. The complex of claim 6 wherein said sequence is selected to be complementary with a target oligonucleotide.

8. A zinc finger peptide complex comprising a zinc finger peptide covalently bound to an oligonucleotide having a preselected nucleobase sequence, wherein said zinc finger peptide comprises SEQ ID No. 1.

9. The zinc finger peptide complex of claim 8 wherein said covalent binding is through a tether.

10. The zinc finger peptide complex of claim 8 wherein said tether is $C_1$ to $C_{10}$ alkyl, alkenyl or alkynyl having up to about four optional substituents.

11. The zinc finger peptide complex of claim 8 wherein said oligonucleotide has a sequence selected to bind specifically to a preselected nucleic acid.

12. A method of selectively cleaving a preselected single stranded RNA comprising contacting said single stranded RNA with a zinc finger peptide complex comprising a zinc finger peptide tethered to a oligonucleotide having a preselected sequence, wherein said zinc finger peptide complex comprises SEQ ID No. 1.

13. A method of selectively cleaving a preselected single stranded RNA comprising contacting said single stranded RNA with a zinc finger peptide complex comprising a zinc finger peptide covalently bound to an oligonucleotide having a nucleotide sequence selected to specifically bind to the preselected single stranded RNA, wherein said zinc finger peptide complex comprises SEQ ID No. 1.

* * * * *

UNITED STATES PATENT AND TRADEMARK OFFICE
CERTIFICATE OF CORRECTION

PATENT NO.   : 6,365,379 B1
DATED        : April 2, 2002
INVENTOR(S)  : Lima et al.

It is certified that error appears in the above-identified patent and that said Letters Patent is hereby corrected as shown below:

Column 9,
Line 5, please delete "RNA-s" and insert therefor -- RNA's --;

Column 14,
Line 19, please delete "Seq. I.D. No.1" and insert therefor -- Seq. I.D. No. 11 --;

Signed and Sealed this

Nineteenth Day of November, 2002

Attest:

Attesting Officer

JAMES E. ROGAN
*Director of the United States Patent and Trademark Office*